United States Patent
Hiernaux et al.

(10) Patent No.: US 11,076,847 B2
(45) Date of Patent: Aug. 3, 2021

(54) DEVICE FOR SUPPORTING AN ENDOSCOPIC TOOL

(71) Applicant: ENDO TOOLS THERAPEUTICS S.A., Gosselies (BE)

(72) Inventors: Martin Hiernaux, Auderghem (BE); Loulia Leclercq, Uccle (BE); Simon Goldstein, Uccle (BE); Alexandre Chau, Ixelles (BE)

(73) Assignee: ENDO TOOLS THERAPEUTICS S.A., Gosselies (BE)

( * ) Notice: Subject to any disclaimer, the term of this patent is extended or adjusted under 35 U.S.C. 154(b) by 91 days.

(21) Appl. No.: 16/619,832

(22) PCT Filed: Apr. 13, 2018

(86) PCT No.: PCT/EP2018/059525
§ 371 (c)(1),
(2) Date: Dec. 5, 2019

(87) PCT Pub. No.: WO2018/228735
PCT Pub. Date: Dec. 20, 2018

(65) Prior Publication Data
US 2020/0129173 A1    Apr. 30, 2020

(30) Foreign Application Priority Data
Jun. 15, 2017    (EP) .................................... 17176240

(51) Int. Cl.
*A61B 17/04*    (2006.01)
*A61B 17/29*    (2006.01)

(52) U.S. Cl.
CPC ...... *A61B 17/0469* (2013.01); *A61B 17/0482* (2013.01); *A61B 17/29* (2013.01)

(58) Field of Classification Search
CPC ......... A61B 17/04; A61B 1/00; A61B 1/0014; A61B 17/0469; A61B 17/0482; A61B 2017/00296; A61B 17/29
See application file for complete search history.

(56) References Cited

U.S. PATENT DOCUMENTS

| 2013/0096581 A1 | 4/2013 | Gilkey et al. | |
| 2016/0235400 A1* | 8/2016 | Hiernaux | G02B 23/2476 |
| 2019/0015172 A1* | 1/2019 | Yamaya | A61B 1/00101 |

FOREIGN PATENT DOCUMENTS

WO    2015/052320 A1    4/2015

OTHER PUBLICATIONS

Jul. 9, 2018, International Search Report and Written Opinion, European Patent Office, in PCT/EP2018/059525, which is the International Application corresponding to this U.S. application.

(Continued)

*Primary Examiner* — George J Ulsh
(74) *Attorney, Agent, or Firm* — Kolitch Romano LLP (57) ABSTRACT

A device for supporting an endoscopic tool may include opposite first and second arms extending along a first axis. An attachment system is configured to attach the first arm and the second arm to an endoscope. A curved guide for the endoscopic tool is coupled to the first arm, and has an outlet for launching the endoscopic tool. An angled tissue support surface is provided on the second arm, facing the outlet. The outlet is fixable in a working orientation relative to the first axis, and in the working orientation, a recess of the tissue support surface is configured to accept the endoscopic tool when launched from the outlet.

20 Claims, 10 Drawing Sheets

(56) References Cited

OTHER PUBLICATIONS

Jun. 21, 2019, International Preliminary Report on Patentability, European Patent Office, in PCT/EP2018/059525, which is the International Application corresponding to this U.S. application.

* cited by examiner

DEVICE FOR SUPPORTING AN ENDOSCOPIC TOOL

FIELD

The present disclosure is related to endoscopic devices for supporting endoscopic surgical tools, in particular tissue suturing needles. Present devices are configured for attachment to an endoscope, for use in endoscopic or laparoscopic surgery.

INTRODUCTION

A device of the above kind is known from WO 2015/052320, 16 Apr. 2015 and comprises opposite first and second projecting members which extend distally of respective attachment members for attaching the device externally to an endoscope. A cable system is linked to the attachment members and allows for moving the attachment members—and, integrally therewith, the projecting members—further apart, or closer to each other. Operating the cable system allows the device to assume different configurations, in particular a first configuration in which the projecting members are moved close to each other to reduce bulkiness of the system, and a second configuration in which the projecting members are spaced apart and an endoscope can be inserted and fixedly held (e.g., clamped) between the attachment members. The first configuration allows the device to be easily inserted inside the patient, in particular through a natural orifice, whereas the second configuration corresponds to an operating configuration. A guide tube has a distal outlet end which is pivotally attached to a distal end of the first projecting member. The guide tube is further slidable along the projecting member, and sliding the guide tube towards the distal outlet end allows for pivoting the outlet end towards the second projecting member allowing a suturing needle to be launched from the outlet end of the guide tube towards the second projecting member.

The above device has proven to operate well in cavities in which there is sufficient space available for deploying the guide tube, such as in the stomach, and for long suturing needles allowing to pierce through relatively thick and tough tissue. In order to pivot the distal end of the guide tube, the guide tube must be slid to assume an S-shape which further increases the bulkiness of the system and therefore requires some additional space within the bodily cavity.

However, in some situations such an additional space is not available, for example in the oesophagus or in case of a gastric reduction following a gastric bypass. In the latter case, it has been observed that following a gastric bypass, the remaining part of the stomach, or part of the intestine dilates over time. In some cases, this may lead to a new surgical intervention being required in order to reduce the dilated part of the stomach or the intestine. Even though the kind of tissue remains the same, i.e. the tissue which has to be sutured is thick and tough and requires exerting larger forces and stronger and longer needles, the available cavity space in which to operate is much smaller compared to the first gastric reduction intervention.

WO 2014/033692, 6 Mar. 2014 describes a suturing device comprising first and second elongate jaws which are rotatable relative to each other. The jaws respectively have first and second longitudinal axes and first and second gripping surfaces for gripping and holding a region of tissue at a tilt angle relative to the first and second axes when the jaws are closed. A channel is disposed in the first elongate jaw having a substantially straight section extending along the first longitudinal axis and a curved section that extends from the straight section to the first gripping surface. A flexible needle is housed inside the channel and carries along one or more suture anchors housed in the straight section of the channel. The needle is controllable to extract a suture anchor in the channel from the first jaw through the curved section and drive the extracted suture anchor through the tissue region to secure the suture thread. The curved section of the channel opens perpendicularly on a face of the first jaw that is tilted with respect to the longitudinal axis by an acute angle greater than or equal to about 30°. The curved section has a minimum radius of curvature between 2.5 mm and 4.5 mm. To negotiate with such minimum radius of curvature, the drive needle and the suture anchors transported by the needle are configured to resiliently bend when transported through the curved section of the channel. A needle backstop is provided at a distal end of the opposite second jaw having a recess and a backstop surface surrounding the recess. The backstop surface is also tilted relative to the longitudinal axis so as to meet the tilted surface of the first jaw.

One disadvantage of the above suturing device is that it can suture only relatively thin tissue layers which can be received between the alligator jaws when closed. Furthermore, due to the minimum radius of curvature of the curved section either short needles or flexible needles must be used but the piercing force that can be exerted with such needles is limited.

SUMMARY

It would therefore be desirable to provide a device enabling a tissue suturing as performant as in WO 2015/052320, while having a reduced bulkiness, and therefore allowing to be used in even the smallest cavities. It would be desirable to provide a device in which long needles can be used but which has a reduced bulkiness, thus allowing suturing of relatively thick and tough tissues in bodily spaces which are difficult to reach.

According to a first aspect of the disclosure, there is therefore provided a device for supporting an endoscopic tool, such as though not limited to a tissue suturing needle, the device comprising:

(i) opposite first and second arms extending along a first axis between a proximal end and a distal end,
(ii) attachment system or means for attachment to an endoscope, the attachment means provided at the proximal end,
(iii) deploying means operable to move the first and second arms relative to each other in a direction cross to the first axis to adjust a spacing between the first and second arms, the deploying means being advantageously operable to translate the first and second arms relative to each other in the specified direction,
(iv) a guide for the endoscopic tool coupled to the first arm, the guide comprising an outlet for launching the endoscopic tool,
(v) a tissue support surface provided on the second arm, facing the outlet, and
(vi) a recess adjacent the tissue support surface and configured for accepting the endoscopic tool when launched from the outlet.

The attachment means are advantageously formed by the first and second arms comprising at the proximal end respective first and second attachment members for attachment to an endoscope, and further by the deploying means being operable to hold the attachment members in a first position attached to the endoscope. The recess is advantageously facing the outlet, and the tissue support surface advantageously arranged at a periphery of the recess.

According to a second aspect, the outlet has a fixed or at least one fixable orientation relative to the first axis, referred to as a working orientation. In this working orientation, a centreline of the guide is at least in part inclined between the proximal end (e.g., the position where the device is attached or attachable to the endoscope) and the outlet, advantageously in a direction towards the tissue support surface. In one aspect, the centreline may be defined in a plurality of ways, each one of them being applicable individually or in combination with any of the other definitions:
(i) a first tangent to the centreline at the outlet is inclined with respect to the first axis at an angle between 15° and 60°, advantageously between 15° and 45°,
(ii) the first tangent to the centreline at the outlet is inclined with respect to a second tangent to the centreline in correspondence with the proximal end (i.e., a position of attachment to the endoscope) at an angle between 15° and 60°, advantageously between 15° and 45°, i.e. the centreline changes direction from the second tangent to the first tangent by an angle between 15° and 60°, advantageously between 15° and 45°, which equals the angular change of direction experienced by the endoscopic tool driven through the guide,
(iii) the centreline is curved between the proximal end and the outlet with a radius of curvature being at least 12.5 mm, advantageously at least 15 mm, advantageously at least 17.5 mm, advantageously at least 20 mm,
(iv) the centreline is curved between the proximal end and the outlet with a curvature which does not change sign.

In cases (i) and (ii) above, the second tangent to the centreline in correspondence with the proximal end (e.g., the position where the device is attached or attachable to the endoscope) is advantageously parallel to the first axis. The first axis is advantageously defined by the direction between the proximal and distal ends of the first and second arms. The first axis may coincide with a longitudinal axis of the endoscope when attached thereto.

According to a third aspect, the tissue support surface and/or the recess project from the second arm in a direction transverse to the first axis. Advantageously, the device comprises a cantilever structure attached to the second arm, the tissue support surface being a surface of the cantilever structure. The cantilever structure advantageously projects from the second arm in a direction towards the first arm. Advantageously, the tissue support surface is oriented at one or more angles between 35° and 85° relative to the first axis, advantageously between 40° and 80°, advantageously between 45° and 75°. Advantageously the tissue support surface is oriented at angles deviating not more than 20° from perpendicular to the first tangent, advantageously deviating not more than 15°. Alternatively, the tissue support surface is oriented at one or more angles between 55° and 120°, advantageously between 65° and 115° relative to the first axis. Third aspects may be provided to devices according to the first aspect, either independently or in combination with second aspects.

Embodiments of the first to third aspects are set out in the appended claims.

According to a fourth aspect, there is provided an assembly for suturing tissue, comprising any of the devices according to the first aspect and a suturing needle. Embodiments of the fourth aspect are set out in the appended claims.

One advantage of the above devices and assemblies is that by bringing the opposing surfaces between which the tissue is locked closer to each other and by inclining the launching orientation of the endoscopic tool accordingly, surprisingly, a very compact device can be obtained during working conditions, yet enabling to providing appropriate stability to the endoscopic tool, such as a suturing needle, when launched. Even though in WO 2015/052320 the needle guide tube can be pivoted to a large range of angles, there is a stability problem when one wants to use the needle guide tube at small angles due to the inherent flexibility of the guide tube which cannot provide appropriate support for launching the needle. Indeed, the angle of the needle guide tube is set by pushing on the tube proximally, setting the entire tube under compression. At small inclination angles, this mechanism is very sensitive to motion of the control handle and of the intermediate section of the guide tube. Therefore, even providing for a stopping member or abutment for the pivot at small angles will not ensure good fixation of the orientation of the guide tube at the outlet. These problems are obviated in devices as described herein, with a working orientation in which the outlet of the guide tube is slightly inclined and the tissue support surface is arranged closer to the outlet, with the outlet fixable or fixed in the specified orientation.

A further advantage is that the centreline of the guide for the endoscopic tool can be kept parallel to the first (longitudinal) axis at the proximal end (e.g., at the attachment position to the endoscope), which minimizes the change of direction of the centreline, between the proximal end and the distal end (outlet). This not only contributes to the compact design, but also enables to use endoscopic tools having long rigid parts, such as suturing needles of e.g. 10 mm-20 mm length. The fixed (or fixable) orientation of the outlet of the guide furthermore contributes to strength and rigidity required when these long tools are used.

Particular embodiments of the first aspect and the second aspect are set out in the appended dependent claims.

In one particular embodiment, the first arm comprises at least one hinged section, or a plurality of consecutively arranged hinged sections. The guide extends through the hinged section. The hinged section can be pivoted to ensure the outlet can be positioned in the working orientation as described. Advantageously, a fixing means, such as a cable, is provided to fix the hinged section(s) in the working orientation.

Methods for suturing tissue making use of devices according to the first aspect and/or assemblies according to the second aspect are described herein as well.

BRIEF DESCRIPTION OF THE DRAWINGS

Aspects of the disclosure will now be described in more detail with reference to the appended drawings which are briefly described below and wherein same reference numerals illustrate same features.

DETAILED DESCRIPTION

In the present description, the terms distal and proximal are used according to the customary practice in the field of endoluminal or minimally invasive surgery. Therefore, the term distal as used herein refers to a direction away from, or at an opposite end of the location where the surgeon operates the medical devices, such as an endoscope. The term proximal as used herein refers to a direction towards or at the location where the surgeon operates the medical devices.

In the present description, the term axial, unless otherwise indicated, refers to a direction locally tangent to the path from the proximal end to the distal end or vice versa.

Figure 1:
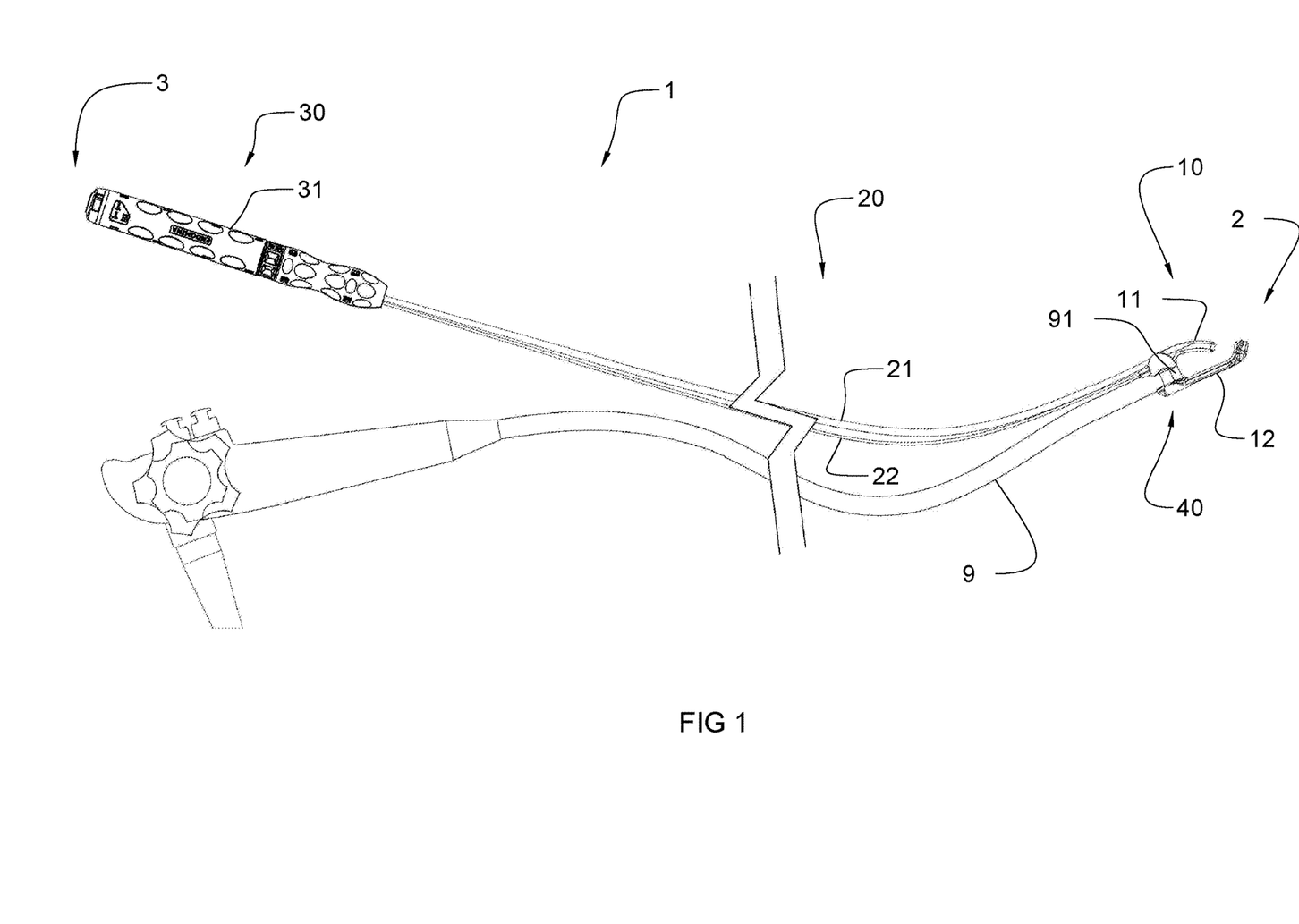
FIG. 1 represents a perspective view of a device for supporting tissue suturing (or other suitable endoscopic interventions) according to aspects described herein when attached to an endoscope.

Referring to FIG. 1, devices 1 for supporting tissue suturing according to aspects described herein comprise a distal section 10 arranged at the distal end 2 of device 1, a proximal section 30 arranged at the proximal end 3 of the device 1 and an intermediate section 20 between the distal section 10 and the proximal section 30. The device 1 comprises at the distal section 10 a pair of arms 11 and 12 arranged oppositely one another and which, in an operating position of the device 1, are attached to an endoscope 9 through an attachment system 40 advantageously enabling the device 12 to removably attach itself to a periphery of the distal tip 91 of endoscope 9. To operate the device 1, manipulating means 31, such as in the form of a control handle are provided at the proximal section 30. The intermediate section 20 advantageously comprises one or more cables or tubes 21, 22 connecting the distal section 10 to the proximal section 30.

Figure 2:
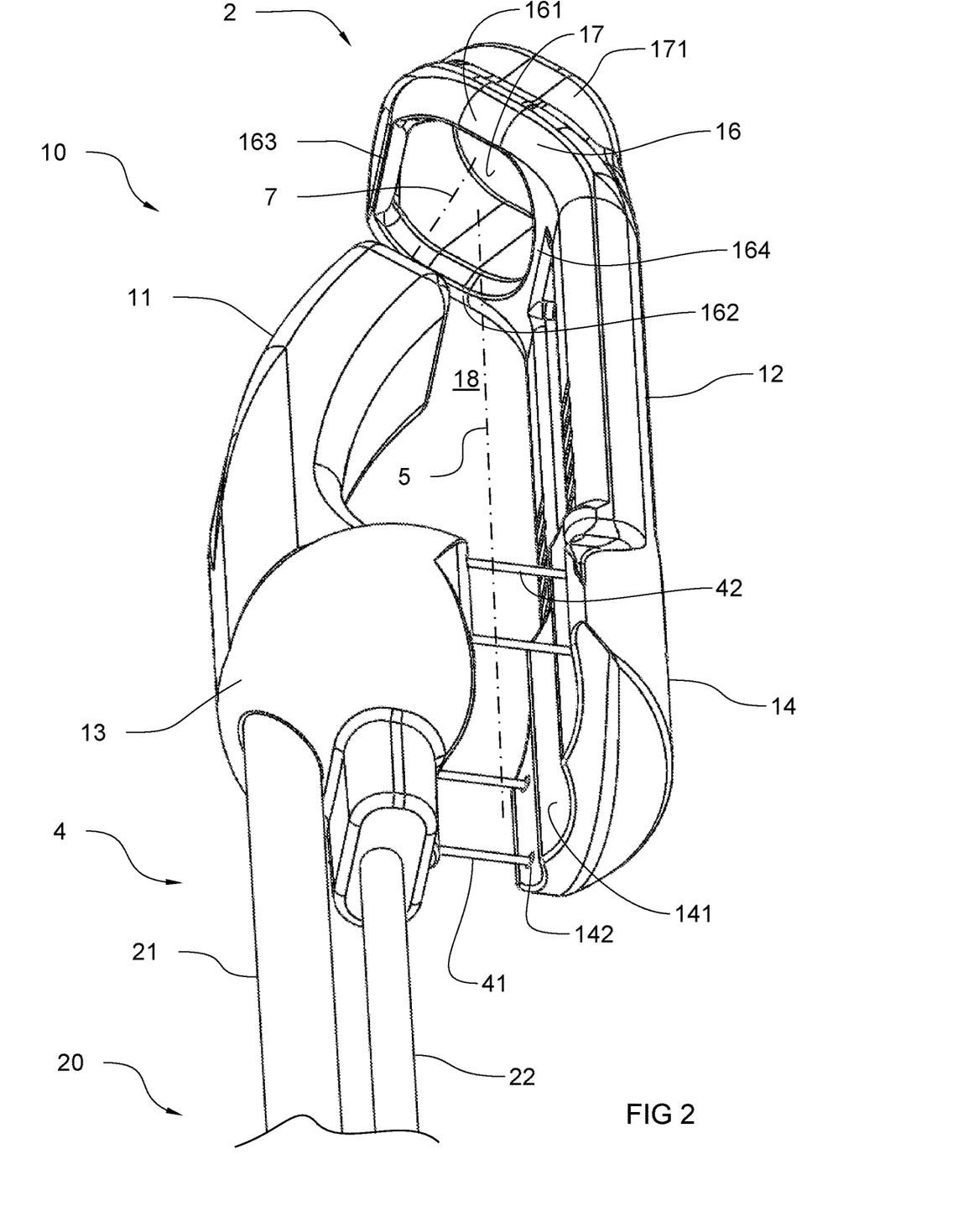
FIG. 2 represents a perspective view of the distal section of the device for supporting tissue suturing of FIG. 1.
Figure 3:
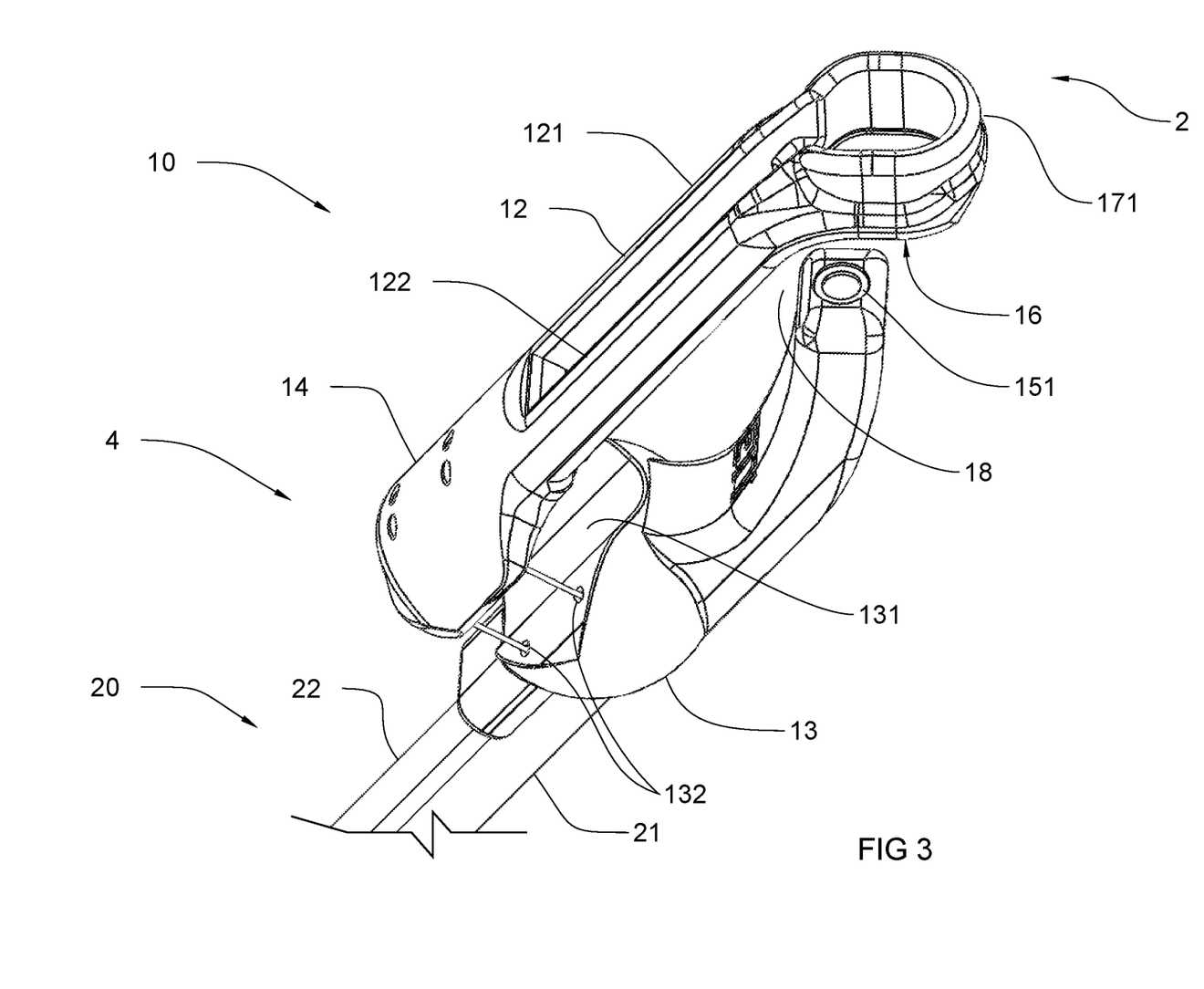
FIG. 3 represents a perspective view of the distal section of FIG. 2 as seen from a different viewing angle.

The distal end 10 of device 1 is shown in greater detail in FIGS. 2 and 3. A first arm 11 and a second arm 12 opposite arm 11 extend along the longitudinal direction of device 1 defined by longitudinal axis 5. In most typical cases, longitudinal axis 5 corresponds to a longitudinal axis of the endoscope 9 to which device 1 is configured to be attached to. Arms 11 and 12 extend form the distal end 2 of the device 1 to a proximal end 4 of the distal section 10, where the distal section is attached to the intermediate section 20.

Each of the arms 11 and 12 comprise at the proximal end 4 respective attachment members 13, 14 which are configured to engage an external part of the endoscope 9, such as the external wall of the endoscope tip 91. To this end, the sides 131, 141 of attachment members 13, 14 which face each other are conveniently shaped to fit a corresponding surface of endoscope 9. By way of example, as shown in FIGS. 2 and 3, inner sides 131, 141 can have a concave shape. The engagement between attachment members 13, 14 and the endoscope can e.g. be a frictional engagement which is maintained by a suitable clamping force exerted by a pair of cables 41, 42. The cables 41, 42 link the attachment members 13, 14 to each other. Either one or both the attachment members 13, 14 comprises one or more cable guide channels 132, 142 for cables 41 and 42. The cables 41 and 42 are guided through these channels and further through a cable guide tube 22 of the intermediate section 20 until control handle 31, from which the cables can be remotely manipulated.

Control handle 31 may for example allow for pushing cables 41 and 42 in the distal direction which causes attachment members 13 and 14, and consequently also arms 11 and 12 to move further apart from one another, in a direction which is advantageously substantially perpendicular to the longitudinal axis 5. Handle 31 may also allow for pulling on cables 41 and 42, such as towards the proximal direction, which causes attachment members 13 and 14 to move towards each other. Pulling on the cables allows the distal section 10 to assume the configuration with minimal bulkiness facilitating endoluminal insertion, before or following insertion of the endoscope 9. Once arrived at the surgical site within a patient, pushing cables 41 and 42 through handle 31 allows for deploying the distal section 10, enabling endoscope 9 to pass between the attachment members 13 and 14. Pulling again on the cables and maintaining the cables in the latter pulled position allows to firmly attach the attachment members 13 and 14 to the endoscope by exerting a suitable clamping, e.g. frictional, force. The cables hence advantageously allow the distal section 10 to be remotely attached to the endoscope 9, e.g. in situ, in the same way as described in WO 2015/052320 referenced hereinabove.

The attachment members 13 and 14, and the cables 41 and 42 together form the attachment system 40. It will be convenient to note that, even though two separate cables are comprised in device 1, it is equally possible to implement the attachment system with only one cable 41 or 42, or more than two cables. Alternatively, the two attachment cables 41, 42 can be replaced by a set of four cables, which pass through cable guide channels 132 in the first attachment member 13 and each cable is attached with one end to the second attachment member 14. It will also be convenient to note that more than two attachment members can be provided. Other remotely actuatable attachment systems, e.g. wherein the cables are replaced by other means, such as by inflatable devices, can be provided in the alternative.

For operating the cables 41, 42, control handle 31 advantageously comprises an actuator being able to move the cables 41 and 42 relative to the cable guide tube 22. Control handle 31 is shown in transparency in FIG. 4 to reveal a possible actuator for operating the cables. Cable guide tube 22 is attached to control handle 31 and guides the four ends of cables 41, 42 to it. Control handle 31 comprises an advantageously elongate housing 50 having a distal end 51 and a proximal end 52. The proximal end of the cable guide tube 22 is secured to the housing, such as at distal end 51. The ends of cables 41 and 42 extend proximally of the cable guide tube and are fixed to a rack 53 which is slidable relative to housing 50. Rack 53 is advantageously housed inside housing 50.

Figure 4:
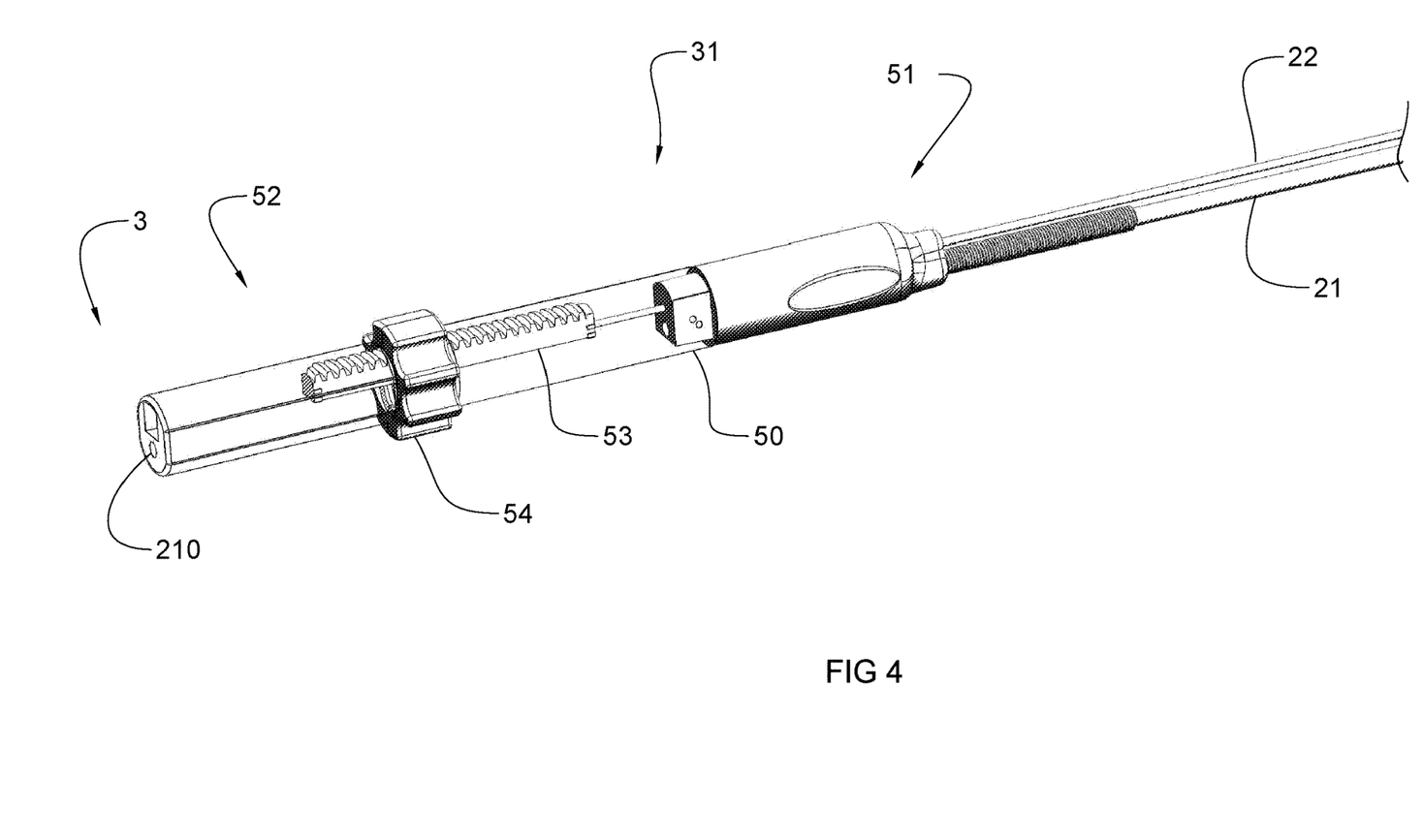
FIG. 4 represents a perspective view of the control handle (proximal section) of the device of FIG. 1, drawn partially in transparency to reveal the inside.

A control ring 54 having an internal worm gear is provided on the housing 50 so as to mesh with the rack 53. Control ring 54 advantageously fits in a recess (not shown) provided in housing 50 which locks all degrees of freedom of control ring 54 other than a rotation on an axis parallel to rack 53. As a result, by turning control ring 54, rack 53 is made to slide relative to the housing 50 and to cable guide tube 22. Control ring 54 can be locked in a specified rotational position relative to the housing 50 by known means, such as a set screw. By so doing, it is possible to operate the attachment members 13, 14 from a remote location. It will be convenient to note that suitable actuators other than the rack and worm gear, such as e.g. pneumatic actuators can be used.

It will be convenient to note that it is advantageous to shape the attachment members such that they are compact in height, which term refers to a linear dimension along the axis of the endoscope or the longitudinal axis 5 over which the attachment member engages the endoscope when in a clamped position. The height of the attachment members advantageously is smaller than or equal to 50 mm, advantageously smaller than or equal to 40 mm, advantageously smaller than or equal to 30 mm, advantageously smaller than or equal to 25 mm. Such a small attachment member preserves the flexibility of the endoscope, in particular at the distal end, so that endoscope positioning during minimally invasive surgery is not hampered. This is important, because most of the endoscope's angulation happens at the distal end.

Referring again to FIGS. 2 and 3, arms 11 and 12 are elongate and fixedly attached to the respective attachment members 13, 14, or alternatively attachable to them in at least one fixable position. Both arms 11 and 12 are advantageously made of a rigid material, such as a polymer or metal, and which is furthermore advantageously biocompatible. Possible polymers are acrylonitrile-butadiene-styrene (ABS), thermoplastic elastomers, such as polyether block amide (PEBA), polyurethane (PU), polyether ether ketone (PEEK), polyamide-imide (PAI), polyethylenimine (PEI), polyphenylsulfone (PPSU), polysulfone (PSU), polyoxymethylene (POM), polycarbonate (PC) and variants. Possible metals are stainless steel 304V, stainless steel 316L, stainless steel 316LVM, titanium and alloys.

Figure 5:
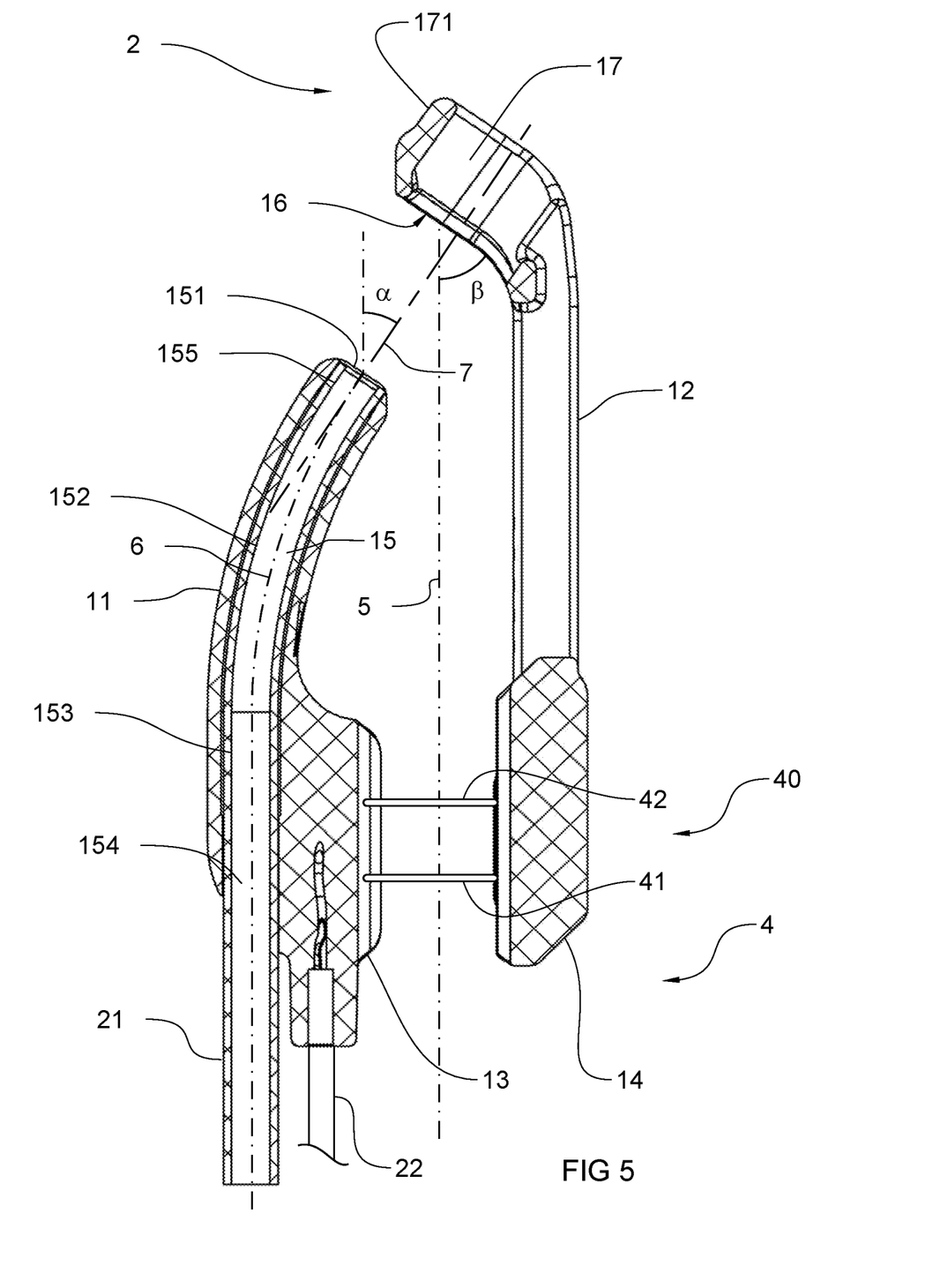
FIG. 5 represents a cross sectional view of the distal section of the device of FIG. 1 along the longitudinal axis, revealing the internal channel for guiding a suturing needle.

Referring now to FIG. 5, the first arm 11 comprises an internal channel 15 extending from the proximal end 4 to the distal end 2 along the longitudinal axis 5 for guiding a suturing needle or other appropriate endoscopic tool. Internal channel 15 comprises a channel outlet 151 at the distal end 2 and a channel inlet 154 communicating with a needle guide tube 21 of the intermediate section 20. Needle guide tube 21 further extends until control handle 31 and is configured to receive a suturing needle which can be driven from the inlet 210 at proximal end 3, through the guide tube 21, to the internal channel 15. Internal channel 15 comprises a curved section 152 adjacent the channel outlet 151 and may further comprise a rectilinear section 153 extending from the curved section to the channel inlet 154. Additionally, or alternatively, internal channel 15 may comprise a rectilinear section 155 between the curved section 152 and the channel outlet 151. Yet alternatively, the curved section 152 may extend along the entire length of the internal channel 15, from inlet 154 to outlet 151. Centreline 6 of the internal channel 15 is curved in the curved section 152, and is straight in the rectilinear sections 153, 155.

In a first aspect, channel 15, and more specifically channel outlet 151 defines an exit direction of the suturing needle out of channel 15. This exit direction may be defined by a tangent 7 to a centreline 6 of the internal channel 15 at the channel outlet. Tangent 7 is advantageously inclined with respect to the longitudinal axis 5 of device 1 at an angle α, advantageously between 15° and 45° in a sense towards the second arm 12. The angle α is advantageously between 20° and 40°, advantageously between 25° and 35°. In some cases, the angle α can be slightly larger, such as between 45° and 55° or between 45° and 60° without loss of functionality. As the structure of the first arm 11 is fixed, it will be appreciated that the angle α advantageously is a fixed angle.

In a second aspect, internal channel 15 advantageously imparts a direction change to suturing needle between channel inlet 154 and channel outlet 151 over an advantageously fixed angle which is between 15° and 45°, advantageously between 20° and 40°, advantageously between 25° and 35°, e.g. over an angle which will be equal to or less than the angle α. It will be appreciated that the direction change can occur over an angle between 45° and 60°. In other words, channel centreline 6 may bend between channel inlet 154 and channel outlet 151 over an angle between 15° and 60°, advantageously between 15° and 55°, advantageously between 15° and 45°, advantageously between 20° and 40°, advantageously between 25° and 35°, e.g. channel centreline 6 advantageously bends over an angle which is equal to or less than a. In particular, a tangent to channel centreline 6 at channel inlet 154, may be parallel to the longitudinal axis 5, or alternatively may be at an acute angle to the longitudinal axis 5 in the same sense as a, and smaller than a.

In a third aspect, centreline 6 of internal channel 15 is curved, e.g. in the curved section 152, with a curvature which does not change sign between the channel inlet 154 and the channel outlet 151. In other words, considered from the channel inlet 154 to the channel outlet 151, the centreline 6 deflects towards the second arm 12 in a monotonic fashion. By way of example, the internal channel 15 does not comprise S-shaped curved sections.

In a fourth aspect, centreline 6 of internal channel 15 is curved, e.g. in the curved section 152, with a radius of curvature which is at least 12.5 mm, advantageously at least 15 mm, advantageously at least 17.5 mm, advantageously at least 20 mm, advantageously at least 25 mm, advantageously at least 30 mm. Suitable values for the radius of curvature of centreline 6 may be less than or equal to 300 mm, advantageously less than or equal to 250 mm, advantageously less than or equal to 150 mm. It will be convenient to note that a radius of curvature of 12.5 mm corresponds to an angle α of about 60° for typical dimensions of the device.

In a fifth aspect, the curved section 152 of internal channel 15 extends over a length, as measured along centreline 6, of at least 3.27 mm, advantageously at least 3.5 mm, advantageously at least 4.0 mm, advantageously at least 5 mm, advantageously at least 6 mm, advantageously at least 7 mm.

It will be convenient to note that any one of the above first to fifth aspects can be provided alone, or in any combination in devices described herein. The curved section may be formed by a sequence of straight sections being progressively inclined to approximate the desired curve. Additionally, as shown in FIG. 5, the needle guide tube 21 may be made to extend substantially until the outlet 151, and act either as lining, or replace the internal channel 15. In the latter case, the first arm 11 is configured to receive the needle guide tube 21 and to curve the tube 21 until outlet 151 in a way substantially as described hereinabove in relation to FIG. 5. The needle guide tube 21 may extend to any one of the sections 153, 152 and 155 and replace the corresponding sections of the internal channel 15.

Figure 6A:
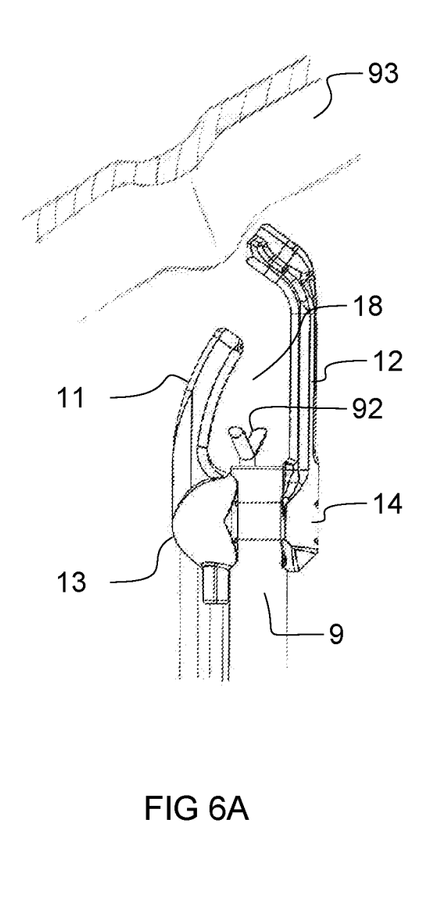
FIG. 6A represents the distal end of FIG. 1 while in use during a first step of a tissue suturing operation.
Figure 6B:
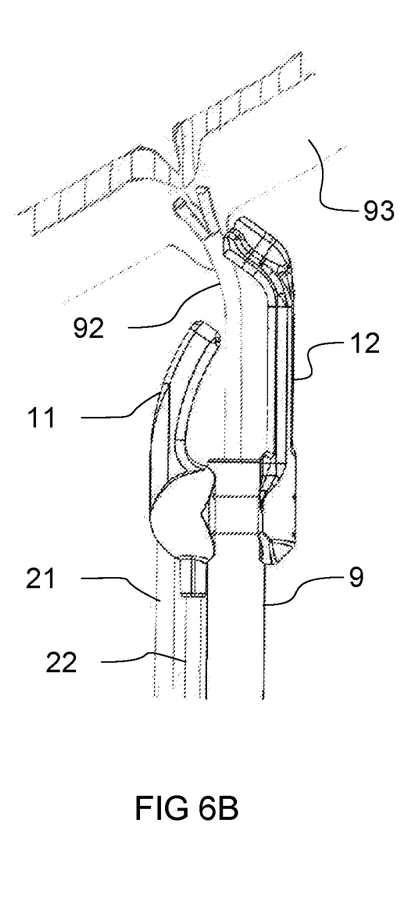
FIG. 6B represents the distal end of FIG. 1 while in use during a second step of the tissue suturing operation.
Figure 6C:
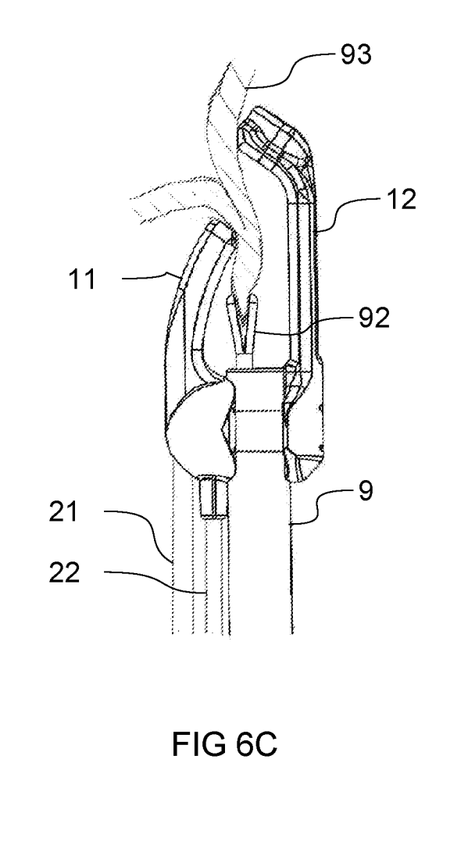
FIG. 6C represents the distal end of FIG. 1 while in use during a third step of the tissue suturing operation.
Figure 6D:
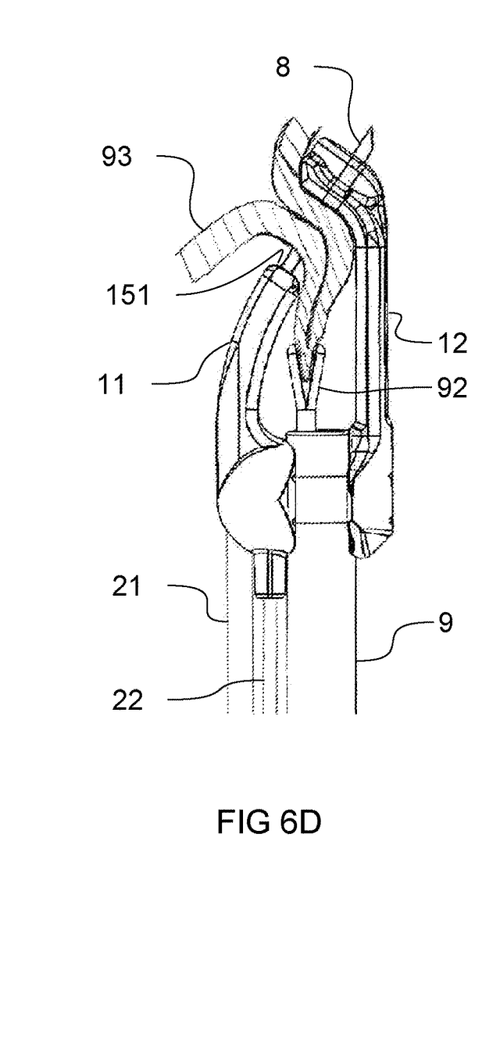
FIG. 6D represents the distal end of FIG. 1 while in use during a fourth step of the tissue suturing operation.
Figure 6E:
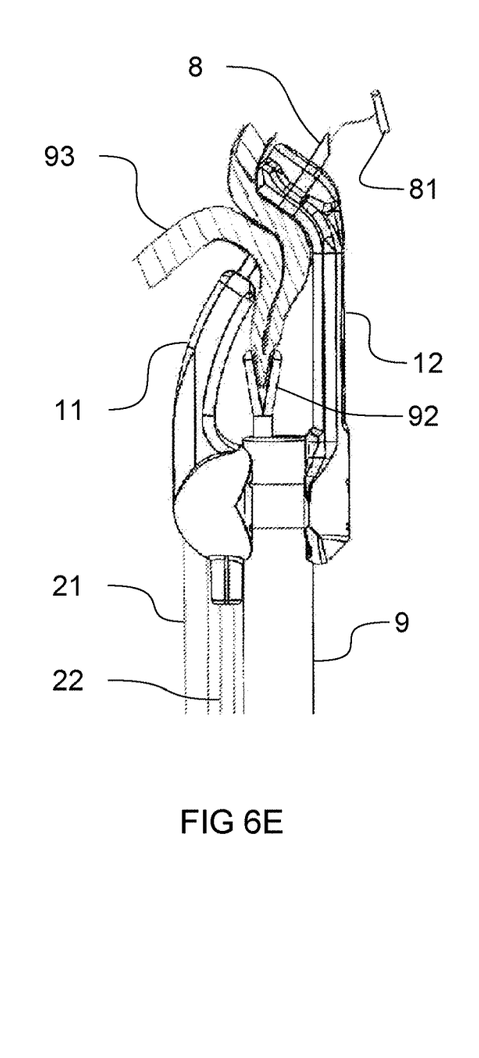
FIG. 6E represents the distal end of FIG. 1 while in use during a fifth step of the tissue suturing operation.

One advantage of the shape of the internal channel 15 described in any one of the above aspects is that the device may remain compact in its deployed configuration, yet allows to drive relatively long suturing needles through it and to provide sufficient backing force during piercing of tissue. Such needles advantageously have a rigid part proximate the needle tip having a length of at least 10 mm, advantageously at least 12 mm, advantageously at least 15 mm, and the rigid part may be between 17 mm and 19 mm long. The compactness of present devices is advantageously obtained by inclining the launch direction of a suturing needle 8 relative to an axis of the endoscope 9, e.g. as shown in FIGS. 6D-E to an acute angle which is considerably less than 90°. By so doing, there is no need to have the needle drive channel (i.e., internal channel 15) assume an S-shape, and/or suturing needles 8 having longer rigid tips can be used. In addition, in the described configuration, the suture operation may still be sufficiently visualised by a camera of the endoscope 9.

The diameter of internal channel 15 may range between 1 mm and 4 mm.

Referring now again to FIGS. 2-3, on the second arm 12, in a position facing the outlet 151 of the internal channel of the first arm 11, there is provided a tissue support surface 16. Tissue support surface 16 advantageously guides pulling of a tissue fold into space 18 between the first arm 11 and the second arm 12. Additionally, or in the alternative, tissue support surface 16 provides backing support of the tissue fold/tissue layer during piercing by a suturing needle which is launched from the outlet 151. The tissue support surface 16 may comprise a first support area 161 and a second support area 162 arranged opposite one another. Opposite third and fourth support areas 163, 164 may join the first support area 161 and the second support area 162 to each other.

The tissue support surface 16 encloses a recess 17 which is so positioned that it is crossed by the tangent 7 to the centreline 6 of the internal channel 15 at outlet 151. Recess 17 therefore will accept the suturing needle after having been launched from channel outlet 151 and after having pierced through the tissue. Recess 17 is advantageously formed by a hole or through-opening through a cantilever structure 171 projecting from arm 12 in a direction transverse, and advantageously oblique, to longitudinal axis 5. Tissue support surface 16 in fact is a surface of cantilever structure 171 facing outlet 151. The cantilever structure 171 has sufficient height to make recess 17 of sufficient depth so as to receive the tip of the suturing needle launched from the outlet 151 and deploy a suturing thread, suture anchor or any other suitable article from the needle, after having pierced the tissue pulled between the first and second arms. Advantageously, recess 17 has a size which is sufficiently large to accommodate different sizes of endoscope 9. By way of example, the size of recess 17 is such that it can accommodate a variability of at least 3 mm, advantageously at least 5 mm on the endoscope diameter, e.g. device 1 may be suitable for endoscopes having a diameter between 7 mm and 12 mm (e.g., as determined at the endoscope tip). In the latter example, with endoscopes smaller than 7 mm, the needle would be blocked by support area 164 and with too large endoscopes, the needle would be blocked by support area 163. Advantageously, the size of recess 17, such as a diameter, e.g. of a largest inscribed circle, is at least 3 mm, advantageously at least 5 mm, advantageously at least 7 mm.

In one aspect, the tissue support surface 16 is inclined with respect to the longitudinal axis 5, advantageously at an angle $\beta$ between 35° and 85°, advantageously between 40° and 80°, advantageously between 45° and 75°. Advantageously, $\alpha-20°\leq\beta\leq\alpha+20°$, advantageously $\alpha-15°\leq\beta\leq\alpha+15°$. Tissue support surface 16 may be substantially planar and may be substantially perpendicular to the tangent 7, i.e. the tissue support surface is advantageously substantially perpendicular to the exit direction of the suture needle from internal channel 15. This provides optimal support for the tissue during piercing. The expression substantially perpendicular may refer to a deviation of +/−15°, or +/−10° from perpendicular. Tissue support surface 16 can be a complex surface (non-planar), in which case at least 30%, advantageously at least 45% of the surface should have a local tangent which is inclined within the range of angles indicated above.

Figure 9:
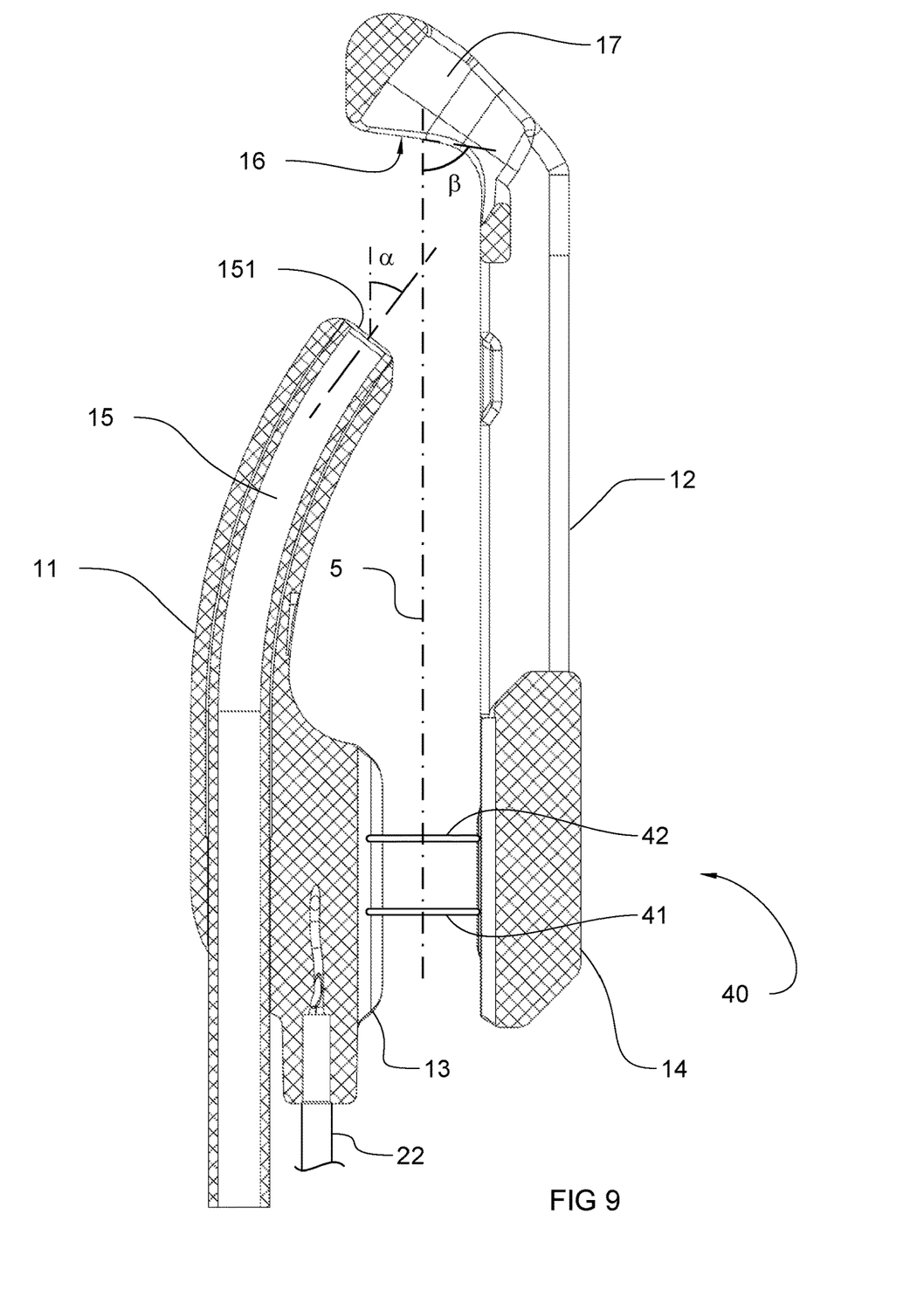
FIG. 9 represents a cross sectional view of an alternative distal section according to aspects described herein, in which the tissue support surface is oriented more or less perpendicular to the longitudinal axis.

In an alternative, advantageous aspect, referring to FIG. 9, the tissue support surface 16 is inclined with respect to the longitudinal axis 5, advantageously at an angle $\beta$ somewhat larger than the complement of angle $\alpha$. It was observed that in some applications, a support surface 16 oriented more or less perpendicular to the longitudinal axis 5 further assists a suturing needle launched from the outlet 151 to maintain the tissue at a stable position relative to the recess 17, therewith reducing the risk that the tissue would slide away from underneath the recess 17 when the needle is piercing the tissue. When tissue is sliding away from underneath the recess 17, the suturing needle has a tendency to follow movement of the tissue and by consequence, the needle tends to bending when following tissue movement. By increasing the angle $\beta$, it was observed that needle bending can be avoided, or at least mitigated. Advantageously, the angle $\beta$ is between 55° and 120° relative to the longitudinal axis 5, advantageously between 65° and 115°. It will be convenient to note that in the present aspect, the angles $\alpha$ and $\beta$ need not, and generally are not, complementary to each other.

In another aspect, the attachment system 40, and in particular the system of cables 41, 42 allows for translating the two attachment members 13, 14 relative to one another. This translation motion is advantageously a linear motion, cross to and advantageously perpendicular to the longitudinal axis 5. One advantage is that the relative orientation between the exit direction of a suturing needle from outlet 151 and the tissue support surface 16 remains invariant when the first and second arms are approached towards each other, or moved further apart. Devices 1 therefore can be attached to endoscopes of differing sizes and tissues of different thicknesses can be pulled/pressed between the arms without loss of functionality.

The second arm 12 comprises one or more uprights 121, 122 which rigidly connect the support surface 16 to the second attachment member 14 to prevent bending of the support surface 16 relative to the first arm 11 during tissue piercing. Uprights 121, 122 advantageously extend substantially parallel to the longitudinal axis 5.

The second arm 12 will generally have a length greater than the length of the first arm 11. That is, the second arm 12 extends distally beyond the distal tip (e.g., the outlet 151) of the first arm 11. In operation, when attached to an endoscope, the spacing between the outlet 151 in the first arm 11 and the tissue support surface 16 of the second arm 12 is advantageously at least 7 mm, advantageously at least 8 mm, advantageously at least 10 mm, and may be even 12 mm or more.

A possible operation of device 1 will now be described with reference to FIGS. 6A-F.

The distal section 10 of the device 1 is made compact, e.g. to facilitate endoluminal insertion. Control ring 54 is turned so as to move the attachment members 13 and 14 towards each other into a configuration with minimal bulkiness. The overall size of the attachment members in the closed position can be selected such that they fit through the smallest endoluminal passage through which they need be inserted. Because the tubes 21, 22 have a smaller footprint than the clamping members, they will not hinder afterwards insertion of the endoscope. Hence, advantageously device 1 is inserted in the patient (such as with the aid of a guidewire), followed by endoscope 9. It will be convenient to note that during insertion, device 1 is not attached to the endoscope 9. Devices described herein can be inserted both endoluminally and laparoscopically, and are particularly suitable for surgical applications requiring transoral endoscopy.

Once arrived at the target location in the patient's body, the distal section 10 is deployed. The control ring 54 is turned to move the attachment members 13, 14 apart and create an opening of sufficient size to enable endoscope 9 to be inserted therein. The distal end of endoscope 9 is inserted between the attachment members from the proximal side and moved distally until a desired position. Next, control ring 54 is turned in the inverse direction to move the attachment members 13, 14 towards each other until they clamp the endoscope 9 between them. Control ring 54 can be locked in position, e.g. by a set screw or by friction. By so doing, as shown in FIG. 6A, a working space 18 is created, which is delimited laterally by the arms 11 and 12, and proximally by the endoscope 9.

A suturing needle 8 is inserted in needle guide tube 21 from the proximal end 3 and pushed until the needle 8 arrives somewhere close the distal section 10, without however protruding from the outlet 151 of the internal channel 15. The device 1 is now ready for operation.

Devices of the present disclosure are advantageously, though not necessarily used for endoscopic suturing. In such cases, the working space 18 is utilized to accept a fold of tissue 93 between arms 11 and 12. Tissue can be pulled in the working space 18 by known surgical tissue engagement tools, such as a piercing helix or graspers 92, which can be provided in a lumen of the endoscope 9 (see FIGS. 6B-C).

Suturing operation can now begin. Referring to FIG. 6D, the suturing needle 8 is advanced through needle guide tube 21 until launched from the outlet 151. During this operation, the tissue support surface 16 on the second arm 12 acts as support for holding the tissue in place.

Any suturing needle as known in the art of minimally invasive surgery can be used in devices of the present disclosure, and well-known suturing techniques can be used.

Figure 6F:
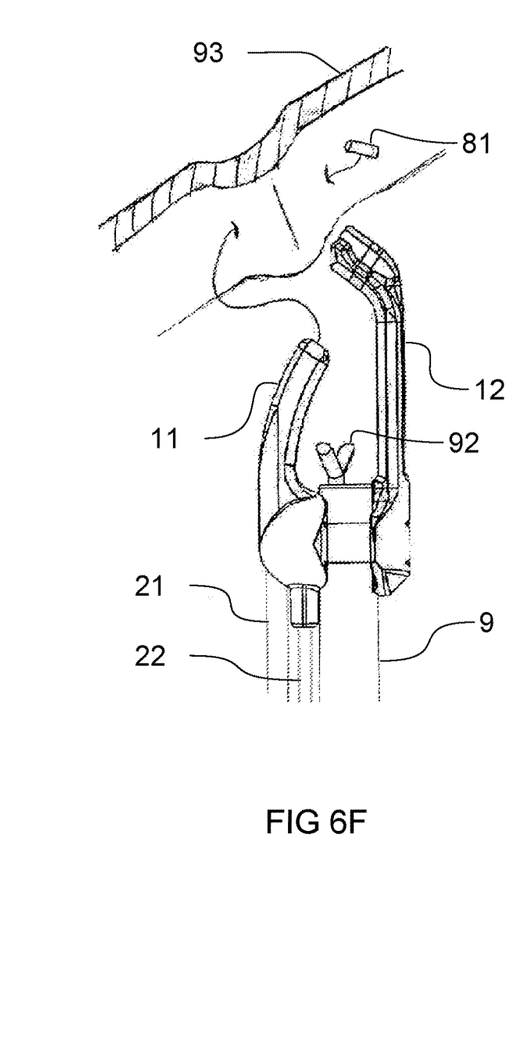
FIG. 6F represents the distal end of FIG. 1 while in use during a sixth step of the tissue suturing operation.

The recess 17 in the second arm 12 advantageously has sufficient depth to house the tip of the suturing needle 8 once having pierced tissue. A suture thread and/or tissue anchor 81 can be deployed from needle 8 in recess 17 (FIG. 6E) and the needle 8 retracted in channel 15 afterwards (FIG. 6F).

Figure 7:
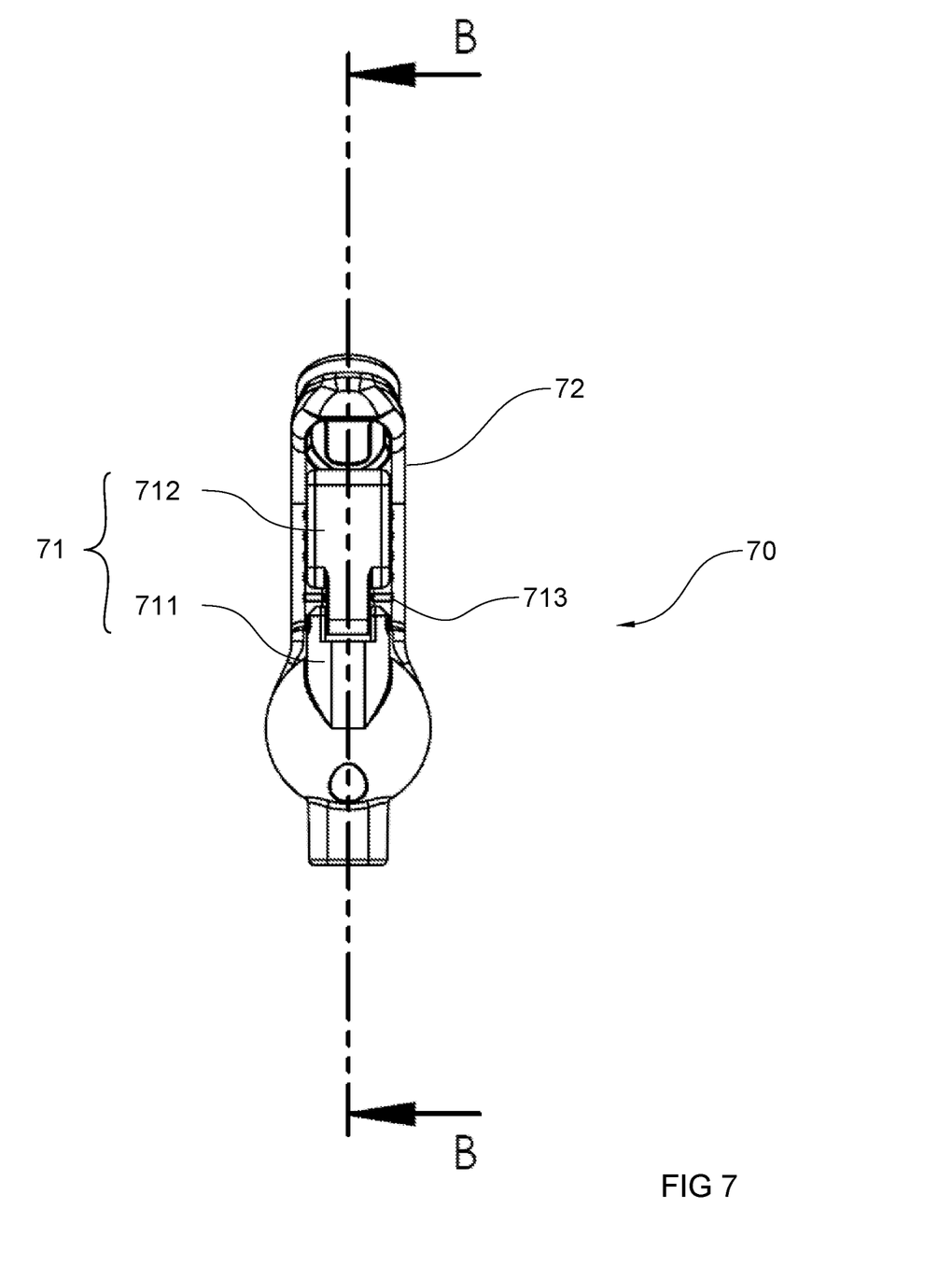
FIG. 7 represents a plan view of the distal section of an alternative embodiment of a device for supporting tissue suturing according to aspects described herein.
Figure 8A:
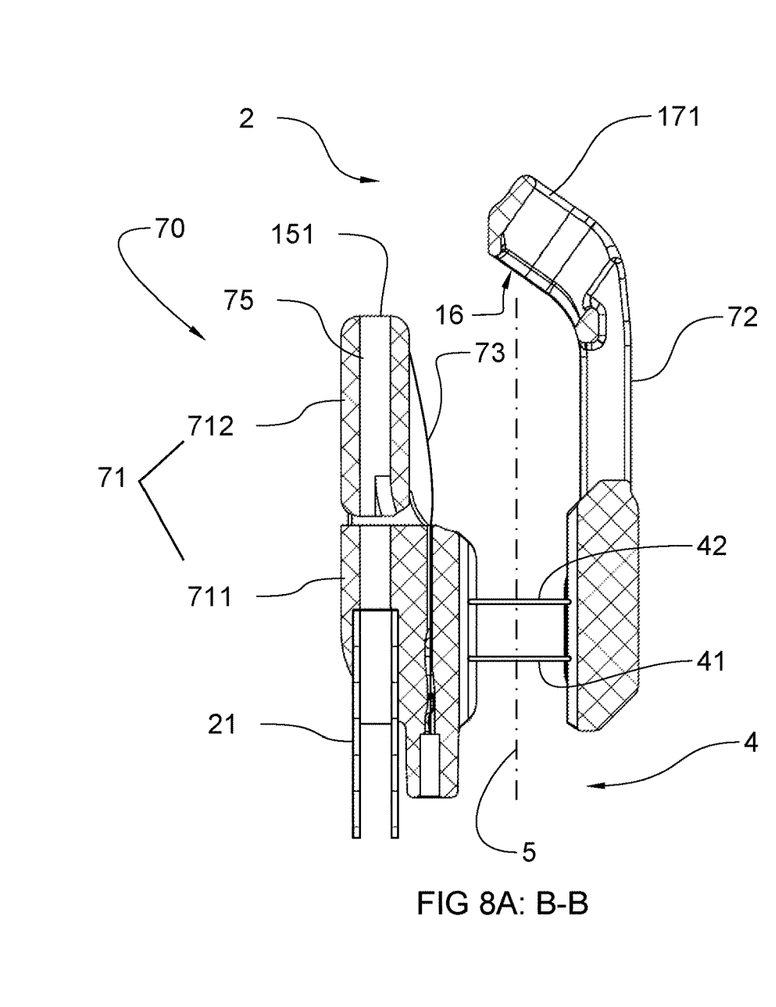
FIG. 8A represents a cross section of the distal section of FIG. 7 along section line B-B (parallel to the longitudinal axis), in a non-working configuration.
Figure 8B:
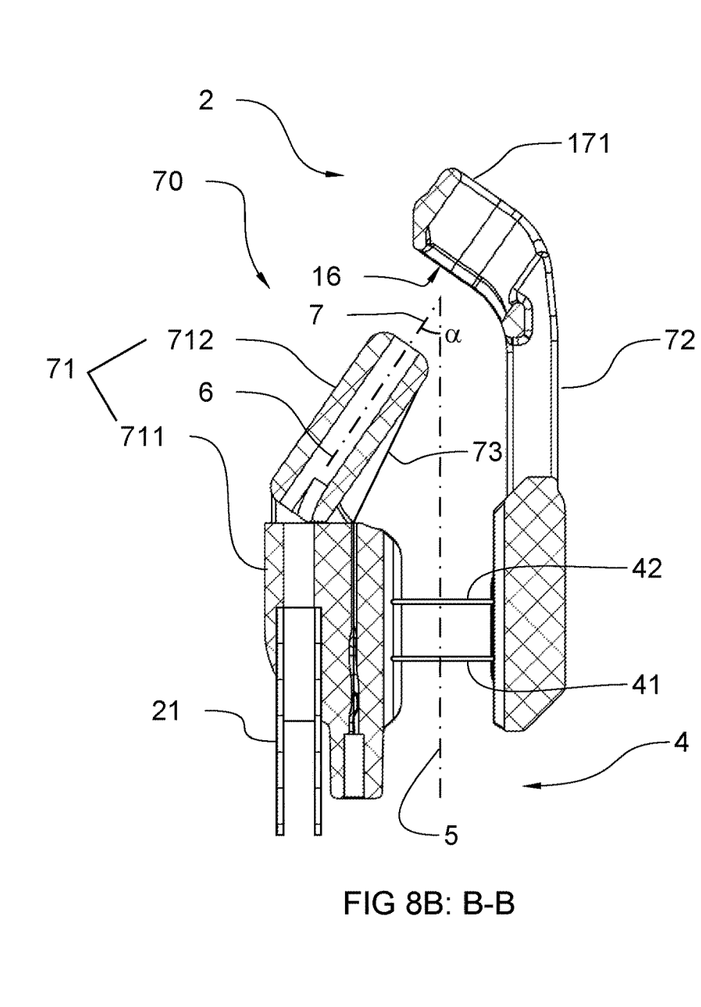
FIG. 8B represents a cross section of the distal section of FIG. 7 along section line B-B (parallel to the longitudinal axis), in a working configuration.

Referring to FIGS. 7 and 8A-B, an alternative embodiment of a distal section 70 of devices for supporting an endoscopic tool is shown. Distal section 70 differs from distal section 10 as described hereinabove in the structure of the first arm 71, while the second arm 72 is substantially the same as arm 12 of FIGS. 2-3. First arm 71 differs from arm 11 of FIGS. 2-3 in that the arm comprises a proximal part 711 and a distal part 712 which is pivotally attached to the proximal part through hinge 713 and extends towards the distal end 2. An internal channel 75 which guides the endoscopic tool to outlet 151 is provided in arm 71 (FIGS. 8A-B). Internal channel 75 extends from the proximal end 4 where it communicates with guide tube 21 through the proximal part 711 and the distal part 712 to outlet 151.

The first arm 71 can assume at least two configurations. In a first, non-working configuration as shown in FIG. 8A, the distal part 712 may substantially extend parallel to longitudinal axis 5 and may extend parallel to the proximal part 711. In this configuration, internal channel 75 may be substantially straight between the proximal part 711 and distal part 712, which assists insertion of the suturing needle 8 through the internal channel 75 until a position corresponding with the distal part 712.

A second, working configuration of arm 71 is shown in FIG. 8B. In this configuration, the distal part 712 of arm 71 is pivoted on hinge 713 towards the second arm 72. In this position, tangent 7 to centreline 6 of channel 75 at outlet 151 is inclined with respect to longitudinal axis 5 at a same angle α as indicated hereinabove, e.g. an angle between 15° and 45°. The angle α is advantageously a fixed angle. Any suitable pivoting system can be utilized to deploy arm 71. By way of example, a wire 73 is attached to the distal part 712, distally of hinge 713. Wire 73 extends to the proximal end 3 of device 70, e.g. through the same cable tube used for cables 41, 42, or a separate tube, from where wire 73 can be actuated by an operator. Pulling on wire 73 will pivot the distal part 712 into the working configuration. As wire 73 will set the angle while being under a tensile force (i.e. by pulling wire 73), small angles as indicated can be set and fixed with much more precision as compared to WO 2015/052320, where the needle guide tube must be pushed to set the angle. Advantageously, a suitable stop member, such as an abutment can be provided as an end stop of the pivotal motion, which has the further advantage that a large amount of force can be put on the wire by the operator, ensuring the distal part 712 is securely fixed in the working position.

One advantage of this configuration, is that the internal channel 75 need not be curved, but may be straight in the non-working configuration to facilitate needle motion through channel 75 until the distal part 712. The distal part 712 can then be easily inclined to launch needle 8 from the desired angle α. Advantageously, the length of distal part 712 is at least equal to the length of the rigid part of the needle 8, e.g. at least 10 mm. The non-working configuration may facilitate insertion of the device through an endoluminal channel and/or may facilitate attachment to an endoscope 9. Alternatively, the distal part 712 may be made up of a plurality of hinged sections, arranged consecutively, and each having an internal channel communicating with the internal channels of the adjacent sections. By so doing, a curved channel shape can be approximated in the working configuration.

It will be convenient to note that devices described herein may be altered for use with endoscopes with lateral vision. In this case, the inner faces 131, 141 of the attachment members 13, 14 may have a modified orientation such that, when attached, the longitudinal axis 5 of the device 1 is inclined to the longitudinal axis of endoscope 9, advantageously at an acute angle, e.g. an angle between 10° and 90°.

It will also be convenient to note that additional guide tubes may be attached to the second arm, e.g. for driving additional endoscopic tools to the second arm, or for flushing and/or insufflation. These may e.g. be tools configured to intercept the suture thread which is launched from within a hollow suture needle (in turn launched from the first arm) within recess 17.

The invention claimed is:

1. A device for supporting an endoscopic tool, the device comprising:
   opposite first and second arms extending along a first axis from a proximal end to a distal end,
   an attachment system configured to attach the first arm and the second arm to an endoscope at the proximal end,
   a deployment system operable to translate the first and second arms relative to each other in a direction cross to the first axis to adjust a spacing between the first and second arms,
   a guide for the endoscopic tool coupled to the first arm, the guide comprising an outlet for launching the endoscopic tool,
   a tissue support surface provided on the second arm, facing the outlet, and
   a recess adjacent the tissue support surface,
   wherein the tissue support surface projects from the second arm in a direction transverse to the first axis,
   wherein the outlet is fixable or fixed in a working orientation relative to the first axis, and in the working orientation, the recess is configured to accept the endoscopic tool when launched from the outlet,
   wherein, in the working orientation, a centerline of the guide is curved between the proximal end and the outlet with a radius of curvature being at least 12.5 mm in a direction towards the tissue support surface, and
   wherein the tissue support surface is oriented at one or more second angles between 35° and 120° relative to the first axis.

2. The device according to claim 1, wherein a first tangent to the centerline at the outlet is inclined with respect to the first axis at a first angle between 15° and 60° towards the tissue support surface.

3. The device according to claim 1, wherein the one or more second angles are between 35° and 85° relative to the first axis.

4. The device according to claim 1, wherein the centerline is curved between the proximal end and the outlet with a curvature which does not change sign.

5. The device of claim 1, wherein the deployment system comprises at least one cable linking the first arm to the second arm, the at least one cable being operable to move the first arm relative to the second arm.

6. The device of claim 1, wherein the first arm and the second arm comprise at the proximal end respective first and second attachment members for attachment to the endoscope, and wherein the deployment system is operable to hold the first and second attachment members in a first position attached to the endoscope.

7. The device of claim 6, wherein the second arm comprises an intermediate section connecting the second attachment member of the second arm and the tissue support surface, wherein the intermediate section extends parallel to the first axis.

8. The device of claim 1, wherein the first arm comprises at least one pivotal hinged section, wherein the guide extends through the pivotal hinged section.

9. An assembly, comprising the device of claim 1 and a suturing needle, wherein the suturing needle comprises a rigid part extending from a tip of the suturing needle, the rigid part having a length of at least 10 mm, and wherein the rigid part is movable through the guide.

10. The device of claim 1, wherein adjacent the distal end, the first arm comprises a channel in a fixed orientation relative to the first axis, wherein the channel extends from the proximal end to the outlet.

11. The device of claim 1, wherein, in a deployed configuration, the second arm extends substantially beyond the first arm in direction of the distal end, wherein a spacing between the outlet and the tissue support surface is at least 5 mm as measured along a first tangent to the centerline of the guide at the outlet.

12. A device for supporting an endoscopic tool, the device comprising:
   opposite first and second arms extending along a first axis from a proximal end to a distal end,
   an attachment system configured to attach the first arm and the second arm to an endoscope at the proximal end,
   a deployment system operable to translate the first and second arms relative to each other in a direction cross to the first axis to adjust a spacing between the first and second arms,
   a guide for the endoscopic tool coupled to the first arm, the guide comprising an outlet for launching the endoscopic tool,
   a tissue support surface provided on the second arm, facing the outlet, and
   a recess adjacent the tissue support surface,
   wherein the tissue support surface projects from the second arm in a direction transverse to the first axis,
   wherein the outlet is fixable or fixed in a working orientation relative to the first axis, and in the working orientation, the recess is configured to accept the endoscopic tool when launched from the outlet,
      wherein, in the working orientation, a first tangent to a centerline of the guide at the outlet is inclined with respect to the first axis at a first angle between 15° and 60° towards the tissue support surface, and
   wherein the tissue support surface is oriented at a second angle between 35° and 120° relative to the first axis.

13. The device of claim 12, wherein the centerline of the guide is curved in the working orientation between the proximal end and the outlet with a radius of curvature being at least 12.5 mm.

14. The device of claim 13, wherein the radius of curvature is at least 20 mm.

15. The device of claim 12, wherein the guide comprises a rectilinear section at the proximal end, and wherein the centerline of the guide between the rectilinear section and the outlet is curved with a curvature which does not change sign.

16. The device of claim 12, wherein adjacent the distal end, the first arm comprises a channel in a fixed orientation relative to the first axis.

17. The device of claim 16, wherein the channel extends from the proximal end to the outlet.

18. The device of claim 16, wherein the channel comprises a rectilinear section at the proximal end, and a curved section between the rectilinear section and the outlet, wherein the curved section comprises a curved centerline having a curvature which does not change sign.

19. The device of claim 16, wherein the guide extends through the channel.

20. The device of claim 12, wherein, in a deployed configuration, the second arm extends substantially beyond the first arm in direction of the distal end, wherein a spacing between the outlet and the tissue support surface is at least 5 mm as measured along the first tangent.

* * * * *